United States Patent [19]

Bostic

[11] 4,344,182
[45] Aug. 10, 1982

[54] X-RAY FILM HOLDER
[75] Inventor: John S. Bostic, Parma Heights, Ohio
[73] Assignee: Joseph E. Belavich, Plant City, Fla.
[21] Appl. No.: 187,441
[22] Filed: Sep. 15, 1980
[51] Int. Cl.³ .............................................. G03B 41/16
[52] U.S. Cl. .................................................. 378/170
[58] Field of Search ........................ 250/475, 478, 479
[56] References Cited
U.S. PATENT DOCUMENTS
2,005,993  6/1935  Heron .................................. 250/479

Primary Examiner—Craig E. Church
Attorney, Agent, or Firm—Porter & Associates Co.

[57] ABSTRACT

An X-ray film holder particularly adapted for use in dental work comprises a first clip which may be secured to a conventional saliva ejector and tongue guard. The film holder includes a generally rectangular spine from which a second, film-holding clip projects on one side, and from which the first clip projects on the other side. In use, the normal placement of the saliva ejector and tongue guard properly positions a piece of X-ray film within the mouth.

7 Claims, 5 Drawing Figures

X-RAY FILM HOLDER

BACKGROUND OF THE INVENTION

1. Field of the Invention

The invention relates to X-ray film holders and, more particularly, to an X-ray film holder particularly adapted for conveniently holding a piece of X-ray film within a patient's mouth during the course of dental work or while the patient is anesthetized.

2. Prior Art

In the course of performing dental work such as root canal work, tooth extraction, and many other types of dental operations, it may be necessary or desirable to take X-rays of a patient's teeth. Typically, a small piece of X-ray film will be carried by a plastic or cardboard frame and will be positioned as desired on the inner side of teeth to be examined. Film holders have been designed so that the patient can use his teeth to clamp the film in place during an X-ray operation. Other holders have been developed so that the X-ray film can be held properly in place without the necessity of the patient using his teeth to clamp the film in place. If nothing else, a simple expedient is to have the patient hold the X-ray film in place with a finger.

The foregoing techniques are effective under most circumstances, but are lacking in other circumstances. For example, it is impossible to have the patient bite down on a film holder during the course of certain work such as root canal work. It also is difficult, if not impossible, for a patient to assist in holding X-ray film in place while anesthetized. In these circumstances, use of the patient's finger, a hemostat, and various special film holders presently in existence are not adequate.

In view of the foregoing difficulties, it is an object of the present invention to provide an X-ray film holder for dental work.

It is a further object of the invention to provide an X-ray film holder which will be easily usable to properly position a piece of X-ray film within a patient's mouth either while dental operations are in progress or while the patient is anesthetized, or both.

It is yet another object of the invention to provide an inexpensive X-ray film holder which will function to properly hold X-ray film in place within a patient's mouth during the course of dental work in progress or while the patient is anesthetized, or both, and which is sufficiently inexpensive that it can be disposed after use.

SUMMARY OF THE INVENTION

The foregoing objects of the invention are accomplished by providing an X-ray film holder which may be attached to a conventional saliva ejector and tongue guard. The holder according to the invention includes a first clip which may be secured to the saliva ejector and tongue guard. The film holder also includes a spine and a second, film-holding clip located on that side of the spine opposite the first clip. The film-holding-clip clamps a piece of X-ray film against the spine to support the film in position during an X-ray operation.

In use, the first clip is secured to the saliva ejector and tongue guard and a piece of X-ray film is clamped in place by the film-holding-clip. The saliva ejector and tongue guard then is secured within the patient's mouth in a conventional manner such that the piece of X-ray film is positioned as desired. X-rays then can be taken without need for the patient's mouth to be closed or for the patient to assist in any way in properly holding the X-ray film in place.

DESCRIPTION OF THE PREFERRED EMBODIMENT

An X-ray film holder 10 according to the invention is shown in FIGS. 1-5. The film holder 10 comprises a generally rectangular, elongate spine 12 having a rounded end 14. The other end of the spine 12 is secured to a block-like base 16.

Figure 1:
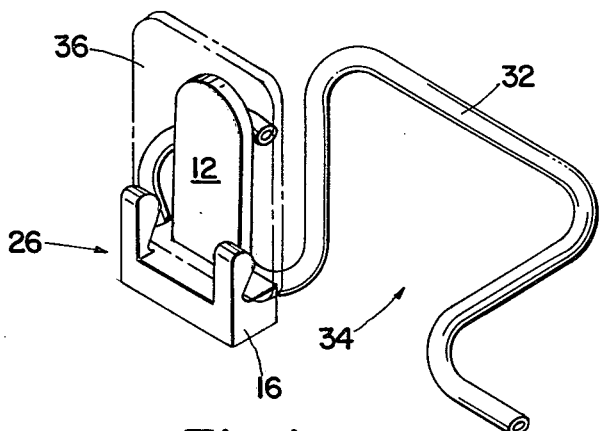
FIG. 1 is a perspective view of an X-ray film holder according to the invention attached to a saliva ejector and tongue guard with a piece of X-ray film being shown by dotted lines.
Figure 2:
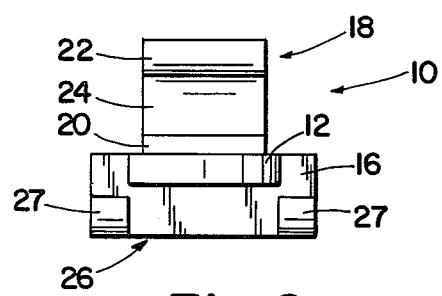
FIG. 2 is a plan view of the X-ray film holder of FIG. 1.
Figure 3:
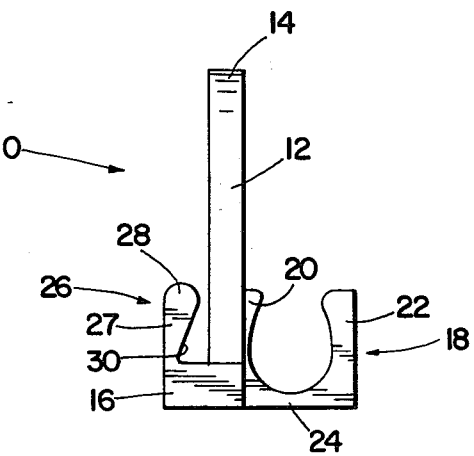
FIG. 3 is an end view of the X-ray film holder of FIG. 1.
Figure 4:
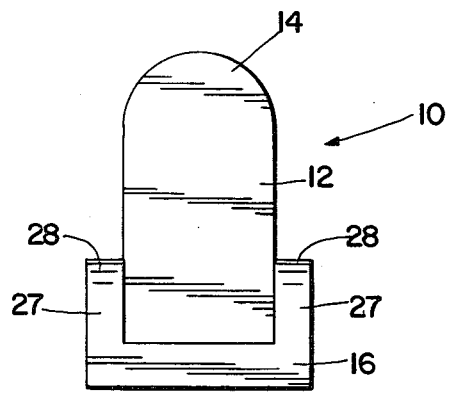
FIG. 4 is a front elevational view of the X-ray film holder of FIG. 1.
Figure 5:
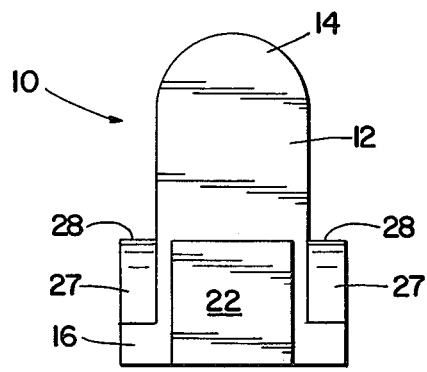
FIG. 5 is a rear elevational view of the X-ray film holder of FIG. 1.

A first clip 18 extends outwardly of the spine 12 near the base 16. The clip 18, when viewed from the end as in FIG. 3, is generally U-shaped and includes a first leg 20, a second leg 22, and an interconnecting region 24. The legs 20, 22 are sufficiently flexible relative to each other that an object can be tightly clamped between them, as will be described.

A second clip 26 projects upwardly from the base portion 16 and includes spaced legs 27 each having a rounded end 28 and an undercut portion 30. The legs 27 are spaced approximately the width of the spine 12 and extend axially in the direction of the longitudinal axis of the spine 12. The legs 27 are sufficiently flexible that they can be moved relative to the spine 12 to clamp objects against the spine 12.

In use, the first clip 18 is secured to an appropriate portion of a conventional saliva ejector and tongue guard 32 having a bight portion 34. A piece of X-ray film 36 can be clamped in place between the legs 27 and the spine 12 either before or after the clip 18 is secured to the saliva ejector and tongue guard 32. Thereafter, the bight portion 34 of the saliva ejector and tongue guard 32 can be secured to a patient's mouth so that the X-ray film 36 can be positioned as desired within the mouth. It will be appreciated that the X-ray film holder 10 according to the invention can be used either with the patient's mouth closed or with the mouth open, and the film will be held properly in place even if the patient is anesthetized or otherwise cannot cooperate in positioning the film.

The X-ray film holder 10 according to the invention is intended to be formed expeditiously in an injection molding process or the like, and it desirably will be made of an inexpensive plastics material. It is intended that the film holder can be thrown away after a single use to avoid the need for repeated sterilization.

Although the invention has been described in its preferred form with a certain degree of particularity, it will be understood that the present disclosure of the preferred embodiment has been made only by way of example and that various changes in the details of construction and the combination and arrangement of parts may be resorted to without departing from the true spirit and scope of the invention as hereinafter claimed.

It is intended that the patent shall cover, by suitable expression in the appended claims, whatever features of patentable novelty exist in the invention disclosed.

What is claimed is:

1. A holder for supporting a piece of X-ray film properly in position within the mouth of a patient during dental operations, comprising:
   (a) a spine forming a central portion of the holder;
   (b) a first clip projecting outwardly of the spine, the first clip adapted for attachment to a saliva ejector and tongue guard; and,
   (c) a second clip projecting outwardly of the spine, the second clip adapted to hold a piece of X-ray film.

2. The film holder of claim 1, wherein the spine is elongate and includes a rounded end.

3. The film holder of claim 1, wherein the second clip includes two legs spaced approximately the width of the spine and extending axially in the direction of the longitudinal axis of the spine.

4. The film holder of claim 1, wherein the holder is formed of plastics material in an injection molding process.

5. A holder for supporting a piece of X-ray film properly in position within the mouth of a patient during dental operations, the holder adapted for attachment to a conventional saliva ejector and tongue guard, comprising:
   (a) an elongate spine forming a central portion of the holder;
   (b) a first clip projecting outwardly of the spine on one side of the spine, the first clip engageable with the saliva ejector and tongue guard; and,
   (c) a second clip projecting outwardly of the spine on the other side of the spine from the first clip, the second clip adpated to hold a piece of X-ray film against the spine.

6. The holder of claim 5, wherein the second clip includes two legs spaced approximately the width of the spine, the two legs extending axially in the direction of the longitudinal axis of the spine.

7. A method for supporting a piece of X-ray film properly in position within the mouth of a patient during dental operations, comprising the steps of:
   (a) securing a piece of X-ray film to an X-ray film holder;
   (b) attaching the X-ray film holder to a saliva ejector and tongue guard; and,
   (c) attaching the saliva ejector and tongue guard to portions of a patient's mouth.

* * * * *